(12) United States Patent
Gellert

(10) Patent No.: US 6,896,406 B2
(45) Date of Patent: May 24, 2005

(54) HEAT CONDUCTIVITY DETECTOR

(75) Inventor: Udo Gellert, Bellheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/691,808

(22) Filed: Oct. 23, 2003

(65) Prior Publication Data

US 2004/0136435 A1 Jul. 15, 2004

Related U.S. Application Data

(63) Continuation of application No. PCT/DE02/01488, filed on Apr. 23, 2002.

(30) Foreign Application Priority Data

Apr. 23, 2001 (DE) .......................................... 101 19 788

(51) Int. Cl.[7] .......................... G01K 17/00; G01N 25/00
(52) U.S. Cl. ........................... 374/44; 374/29; 73/25.03
(58) Field of Search ................................. 374/44, 4, 29, 374/43, 55, 5, 45, 208; 422/82.01, 82.02, 90; 73/23.25, 25.01, 25.03; 436/149

(56) References Cited

U.S. PATENT DOCUMENTS

| | | | | |
|---|---|---|---|---|
| 3,243,991 A | * | 4/1966 | Konig et al. ................ 73/25.03 |
| 3,315,517 A | * | 4/1967 | Konig et al. ................ 73/25.04 |
| 3,416,373 A | * | 12/1968 | Havens ........................... 374/6 |
| 3,537,914 A | * | 11/1970 | Cieplinski et al. ........... 148/281 |
| 3,777,366 A | | 12/1973 | Kiefer |
| 3,888,110 A | | 6/1975 | Clark |
| 4,232,543 A | * | 11/1980 | Eguchi et al. ................ 374/44 |
| 4,254,654 A | * | 3/1981 | Clouser et al. ............... 73/23.4 |
| 4,594,879 A | * | 6/1986 | Maeda et al. ............... 73/25.04 |
| 4,738,544 A | * | 4/1988 | Setier et al. ................... 374/33 |
| 4,766,760 A | * | 8/1988 | Poshemansky et al. ..... 73/23.35 |
| 4,850,714 A | * | 7/1989 | Wiegleb ........................ 374/44 |
| 4,856,319 A | * | 8/1989 | Golay ........................ 73/23.35 |
| 5,081,869 A | * | 1/1992 | Hachey et al. ............. 73/25.03 |
| 5,356,819 A | * | 10/1994 | Ritschel ....................... 436/147 |
| 6,071,008 A | * | 6/2000 | Hatta et al. ................... 374/31 |
| 6,086,251 A | * | 7/2000 | Stark ........................... 374/179 |
| 6,361,204 B1 | * | 3/2002 | Marzoli et al. ............... 374/44 |
| 6,550,961 B1 | * | 4/2003 | Ueda ........................... 374/44 |
| 6,623,976 B1 | * | 9/2003 | Hale et al. .................. 436/160 |
| 6,647,779 B2 | * | 11/2003 | Ishiguro et al. ........... 73/204.26 |
| 6,837,614 B2 | * | 1/2005 | Lee et al. ..................... 374/25 |
| 2004/0250601 A1 | * | 12/2004 | Lin ............................ 73/25.03 |

FOREIGN PATENT DOCUMENTS

| | | |
|---|---|---|
| DE | 1 092 698 | 11/1955 |
| DE | 198 08 681 A1 | 9/1999 |
| GB | 1024869 | 4/1966 |
| JP | 05135850 A * | 6/1993 ............ H05B/3/00 |
| JP | 05232052 A * | 9/1993 .......... G01N/25/18 |
| JP | 10142212 A | 5/1998 |

* cited by examiner

*Primary Examiner*—Gail Verbitsky
(74) *Attorney, Agent, or Firm*—Sughrue Mion, PLLC

(57) ABSTRACT

A thermal conductivity detector with an electrically heatable heating filament (6) that is mounted in the middle of a channel (5) in such a way that a fluid can flow around it. The heating filament is carried on its two ends on two electrically conductive carriers (7, 8) that intersect this channel. In particular to prevent the heating filament from relaxing at operational temperatures, at least one of the two carriers (7, 8) is embodied in such a way that its distance from the other carrier is greater in the region of the middle of the channel than in the region of the wall of the channel (9). As a result, as the temperature rises, the middle areas of the two carriers (7, 8) on which the heating filament (6) is held move away from each other, so that the heating filament (6) is tightened.

14 Claims, 1 Drawing Sheet

HEAT CONDUCTIVITY DETECTOR

This is a Continuation of International Application PCT/DE02/01488, with an international filing date of Apr. 23, 2002, which was published under PCT Article 21(2) in German, and the disclosure of which is incorporated into this application by reference.

FIELD OF AND BACKGROUND OF THE INVENTION

Thermal conductivity detectors are used to detect certain liquid or gaseous substances (fluids) on the basis of their characteristic thermal conductivity, particularly in gas chromatography. For this purpose, the substances to be detected, after their chromatographic separation, are successively guided past an electrically heated heating filament disposed in a channel. Depending on the thermal conductivity of the substance flowing past, more or less heat is diverted from the heating filament to the channel wall, and the heating filament is correspondingly cooled to a greater or lesser degree. As a result of the cooling of the heating filament, its electrical resistance changes, which is detected. For this purpose, the heating filament is typically disposed in a measuring bridge, which contains additional resistors and an additional heating filament in a further channel through which a reference fluid flows.

To detect very small amounts of substances with great sensitivity and accuracy requires a correspondingly small structure of the thermal conductivity detector. Micromechanical production methods are particularly suitable for this purpose. Due to the small overall size, however, special problems are encountered. For example, the heating filament, which is under tension at an ambient temperature, may relax as a result of its thermal expansion at operating temperatures ranging from 100° C. to 200° C. and above. The relaxed filament may then cause the fluid flowing through the channel to then induce vibrations in the heating filament, which increase the detector noise of the thermal conductivity detector and thereby decrease the detection limit. These vibrations may also cause premature fracturing of the very thin heating filament.

OBJECTS OF THE INVENTION

Accordingly, one object of the invention is to provide an improved thermal conductivity detector. Another object is to provide a thermal conductivity detector that reduces or eliminates the particular problems addressed above.

SUMMARY OF THE INVENTION

According to one formulation of the invention, these and other objects are addressed by a thermal conductivity detector with an electrically heatable heating filament that is mounted in a central region of the channel, such that the fluid can flow around it. To this end, it is mounted at its two ends on two electrically conductive carriers intersecting the channel. At least one of the two carriers is configured in such a way that its distance from the other carrier is greater in the region of the channel center than in the region of the channel wall.

This special configuration of at least one carrier, preferably both carriers, causes the center regions of the two carriers on which the heating filament is mounted by its two ends to move away from one another as the temperature increases and thereby to tighten the heating filament. Thus, the heating filament advantageously remains in the center of the channel, so that the measuring characteristics of the thermal conductivity detector do not change.

The relaxation of the heating filament as the temperature increases is counteracted particularly effectively if the at least one carrier is at least approximately V-shaped in its region that intersects the channel.

To achieve the greatest possible thermal expansion in the at least one carrier in order to tighten the heating filament, the corresponding carrier is preferably made exclusively of metal. In other words, the carrier is not fabricated from a carrier substrate made of a material with low thermal expansion, such as silicon dioxide, to which a conductive film is applied.

It is very difficult in practice to compensate completely the heat-related longitudinal expansion of the heating filament by the thermal expansion of the carriers, even if configured according to the invention. The unheated heating filament is therefore preferably held under sufficient tension between the two carriers so that the heating filament is still subject to some tension even when operating temperatures are reached. This would not be possible with carriers that are not configured according to the invention because the tension of the unheated heating filament would have to be set so high that the heating filament would break, or it would have to be made more stable and thus thicker.

Particularly in view of a micromechanical production of the thermal conductivity detector according to the invention, the carriers holding the heating filament are preferably formed on a carrier plate that is provided with a groove. The channel is formed by this groove and an additional groove made in a cover plate that is placed on the carrier plate.

BRIEF DESCRIPTION OF THE DRAWINGS

The invention will now be described in greater detail, by way of example, with reference to an embodiment of the thermal conductivity detector according to the invention, as depicted in the figures, in which.

DETAILED DESCRIPTION OF THE PREFERRED EMBODIMENTS

Figure 1:
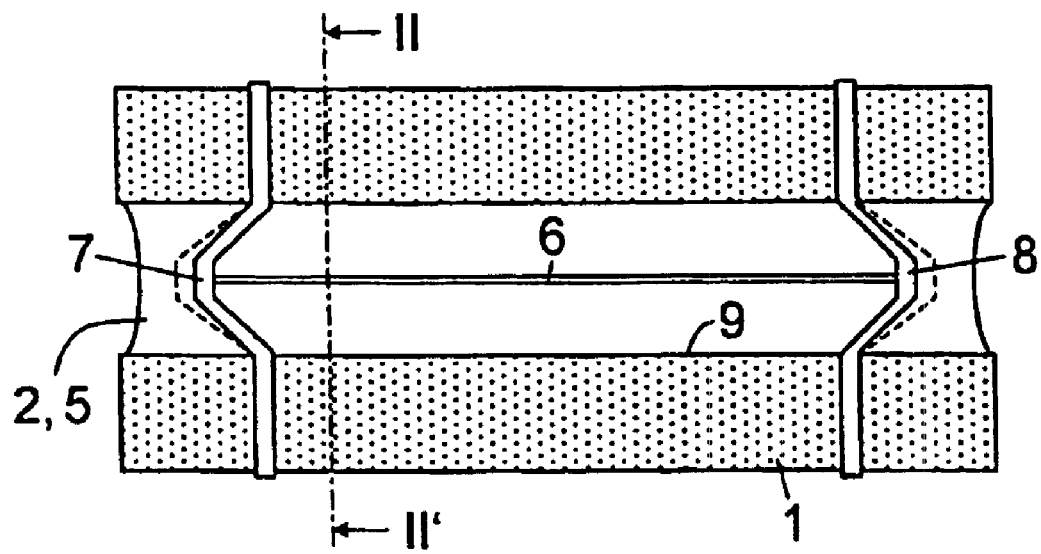
FIG. 1 is a longitudinal section (I–I') of the thermal conductivity detector.
Figure 2:
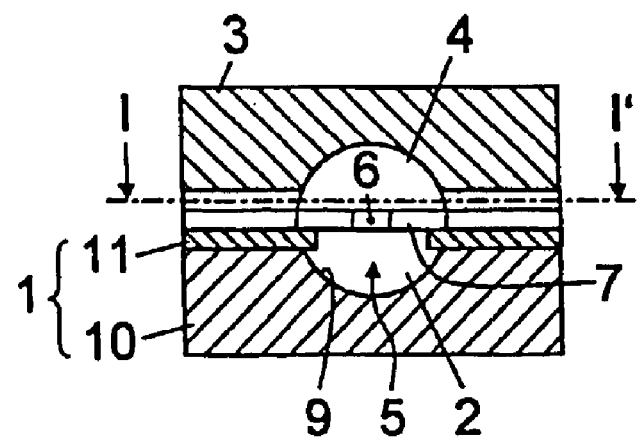
FIG. 2 shows the same thermal conductivity detector in cross section (II–II').

A carrier plate 1 with a groove 2 is covered by a cover plate 3 with an additional groove 4, such that the two grooves 2 and 4 together form a channel 5. The channel 5 preferably has a circular cross section. A heating filament 6 extends longitudinally along the center of the channel 5. The filament 6 is held at its two ends on two electrically conductive carriers 7 and 8, which intersect the channel 5. Each of the two carriers 7 and 8 is configured in such a way that its distance from the respective other carrier in the region of the center of the channel 5, i.e., where the heating filament 6 is mounted, is greater than in the region of the channel wall 9. To this end, the two carriers 7 and 8 are substantially V-shaped here, in their areas intersecting the channel 5, such that the two sides of each V-shaped carrier 7 and 8 extend at an approximately 45° angle to the channel wall 9.

In its unheated state the heating filament 6 is held between the carriers 7 and 8 at a predefined tension. To heat the heating filament 6, an electric current is applied via the two carriers 7 and 8. The reduced tension resulting from the heat-related longitudinal expansion of the heating filament 6 is partly compensated because the central areas of the two carriers 7 and 8 on which the heating filament 6 is mounted move away from one another as the temperature increases, so as to tighten the heating filament 6 (see dashed lines). The tension of the unheated filament 6 is adjusted such that the heating filament 6 is still under a tension $\geq 0$ at operating temperatures, i.e., in the range of 100° C. to 200° C. In other words, it preferably does not become slack. However, the preset tension value of the unheated heating filament 6 can be lower by the amount of the compensation of the tension reduction. For example, if the tension reduction of the heated heating filament 6 is compensated by 40%, only the remaining 60% would need to be compensated when the tension of the unheated heating filament 6 is adjusted.

In this preferred embodiment, for the micromechanical production of the thermal conductivity detector, the carrier plate 1 is initially made of a silicon substrate 10, which carries an insulating layer 11 of silicon dioxide on one side. Metal layers are subsequently applied to this insulating layer 11, (e.g., titanium, chromium, platinum, gold), which on the one hand (gold and/or platinum) subsequently form the carriers 7 and 8 and the heating filament 6 and, on the other hand, act as a bonding agent (titanium, chromium) or a reinforcement (gold) of the layers. In etching processes, the carriers 7 and 8 and the heating filament 6 are formed by structuring the metal layers, and the groove 2 is made in the carrier plate 1. When the carriers 7 and 8 are formed, the insulating layer 11 as the substrate for the carriers 7 and 8 is eliminated as far as possible, such that the carriers consist only of metal and thus can freely expand when heated. Finally, the carrier plate 1 and the cover plate 3 are joined, such that the grooves 2 and 4 that have been made therein form the channel 5. The channel diameter is approximately 0.15 mm, the length of the heating filament is approximately 1 mm and the diameter of the heating filament is <1 $\mu$m.

The above description of the preferred embodiments has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the spirit and scope of the invention, as defined by the appended claims, and equivalents thereof.

What is claimed is:

1. A thermal conductivity detector, comprising:
   a channel wall forming a channel;
   two electrically conductive carriers traversing the channel; and
   an electrically heatable heating filament, which is mounted in a central region of the channel so a fluid in the channel flows around the filament, and is held at ends of the filament on the two electrically conductive carriers,
   wherein at least one of the two carriers is configured such that a minimum distance to the other carrier is larger in the central region of the channel than in a region nearer to the channel wall.

2. The thermal conductivity detector as claimed in claim 1, wherein the at least one carrier has an at least approximately V-shaped section within the channel.

3. The thermal conductivity detector as claimed in claim 1, wherein the at least one carrier consists essentially of metal.

4. The thermal conductivity detector as claimed in claim 1, wherein unheated heating filament is held under tension between the two carriers, and remains under tension at an operating temperature of the detector.

5. The thermal conductivity detector as claimed in claim 1, further comprising:
   a carrier plate supporting the carriers that hold the heating filament, and
   a cover plate placed on the carrier plate,
   wherein the channel is formed by a groove in the carrier plate and an additional groove in the cover plate.

6. The thermal conductivity detector as claimed in claim 1, wherein each of the two carriers is configured such that a minimum distance to the other carrier is larger in the central region of the channel than in a region nearer to the channel wall.

7. The thermal conductivity detector as claimed in claim 1, wherein the filament is a straight filament.

8. The thermal conductivity detector as claimed in claim 1, wherein the at least one of the two carriers is configured to hold a straight filament.

9. The thermal conductivity detector as claimed in claim 1, wherein the two carriers are configured to counteract slacking of the filament.

10. The thermal conductivity detector as claimed in claim 1, wherein the two carriers intersect the channel.

11. The thermal conductivity detector as claimed in claim 10, further comprising:
    a carrier plate supporting the carriers that hold the heating filament, and
    a cover plate placed on the carrier plate,
    wherein each of the two carriers are attached to the carrier plate and the cover plate so as to intersect the channel supporting the filament.

12. A thermal conductivity detector, comprising:
    a channel wall forming a channel;
    two electrically conductive carriers traversing the channel; and
    an electrically heatable heating filament suspended between central regions of the conductive carriers,
    wherein at least one of the conductive carriers has a concavity in at least the central region of the at least one conductive carrier.

13. The thermal conductivity detector as claimed in claim 12, wherein each of the conductive carriers has a concavity in at least the central region of the at least one conductive carrier.

14. A thermal conductivity detector, comprising:
    two electrically conductive carriers mounted in a channel; and
    an electrically heatable heating filament suspended in an area extending between central regions of the conductive carriers,
    wherein at least one of the conductive carriers is mounted to distend away from the area when the detector temperature rises to an operating temperature.

* * * * *